(12) United States Patent
Milhous et al.

(10) Patent No.: US 12,420,062 B2
(45) Date of Patent: Sep. 23, 2025

(54) ELECTRICAL CATHETER

(71) Applicant: MicroVention, Inc., Aliso Viejo, CA (US)

(72) Inventors: Parker Milhous, Santa Ana, CA (US); Heath Bowman, Trabuco Canyon, CA (US); Kaushik Joshi, Tustin, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 53 days.

(21) Appl. No.: 18/431,254

(22) Filed: Feb. 2, 2024

(65) Prior Publication Data

US 2024/0173518 A1    May 30, 2024

Related U.S. Application Data

(63) Continuation of application No. 17/348,571, filed on Jun. 15, 2021, now Pat. No. 11,925,772, which is a continuation of application No. 15/901,720, filed on Feb. 21, 2018, now Pat. No. 11,083,872.

(60) Provisional application No. 62/461,673, filed on Feb. 21, 2017.

(51) Int. Cl.
*A61M 25/00*    (2006.01)
*A61B 18/00*    (2006.01)
*A61B 18/08*    (2006.01)
*A61B 18/14*    (2006.01)
*A61M 39/10*    (2006.01)

(52) U.S. Cl.
CPC ......... *A61M 25/0097* (2013.01); *A61B 18/08* (2013.01); *A61B 18/1492* (2013.01); *A61M 39/10* (2013.01); *A61B 2018/00178* (2013.01); *A61M 2039/1022* (2013.01); *A61M 2205/0272* (2013.01); *A61M 2205/52* (2013.01); *A61M 2205/8206* (2013.01)

(58) Field of Classification Search
None
See application file for complete search history.

(56) References Cited

U.S. PATENT DOCUMENTS

| | | | |
|---|---|---|---|
| 7,255,693 B1 | 8/2007 | Johnston et al. | |
| 7,311,526 B2 | 12/2007 | Rohrbach et al. | |
| 8,497,953 B2 | 7/2013 | Miyamoto et al. | |
| 9,119,551 B2 | 9/2015 | Qi et al. | |
| 9,808,599 B2 | 11/2017 | Bowman et al. | |

(Continued)

FOREIGN PATENT DOCUMENTS

| | | |
|---|---|---|
| CN | 104518351 A | 4/2015 |
| WO | WO 2001/036017 A2 | 5/2001 |
| WO | WO 2017/009539 A1 | 1/2017 |

OTHER PUBLICATIONS

European Patent Office, Supplementary Extended European Search Report dated Nov. 9, 2020 in European Patent Application No. 18757321.7, 9 pages.

(Continued)

*Primary Examiner* — Bernard Rojas
(74) *Attorney, Agent, or Firm* — Inskeep IP Group, Inc.

(57) ABSTRACT

A powered catheter and/or powered catheter system is described. The catheter includes a catheter hub with one set of contact components that are configured to connect to a mating cable with a corresponding second set of contact components. The mating cable can be part of another device, such as a controller or power source.

15 Claims, 15 Drawing Sheets

(56) References Cited

U.S. PATENT DOCUMENTS

| | | |
|---|---|---|
| 10,122,116 B2 | 11/2018 | Troufflard et al. |
| 10,348,027 B2 | 7/2019 | Zhao |
| 2003/0045134 A1 | 3/2003 | Downing |
| 2009/0240121 A1 | 9/2009 | Bickoff |
| 2009/0275815 A1 | 11/2009 | Bickoff et al. |
| 2009/0306655 A1* | 12/2009 | Stangenes ......... A61M 25/0069 606/41 |
| 2010/0069855 A1 | 3/2010 | Ross |
| 2011/0171837 A1 | 7/2011 | Hardisty et al. |
| 2013/0296729 A1 | 11/2013 | Datta |
| 2014/0180280 A1 | 6/2014 | Sigmon, Jr. |
| 2015/0094713 A1* | 4/2015 | Pham .................... H01R 13/64 606/41 |
| 2015/0173773 A1 | 6/2015 | Bowman et al. |
| 2016/0345904 A1 | 12/2016 | Bowman |
| 2017/0172652 A1 | 6/2017 | Govari et al. |
| 2019/0070390 A1 | 3/2019 | Isaacson et al. |

OTHER PUBLICATIONS

WIPO, U.S. International Search Authority, International Search Report and Written Opinion mailed May 3, 2018 in International Patent Application No. PCT/US2018/019032, 10 pages.

Samtec, "Tolc Series Datasheet", Samtec Catalog, Oct. 10, 2017, accessed Apr. 4, 2018, url <suddendocs.samtec.com/catalog_english/tolc.pdf>.

China Patent Office, Office Action dated Nov. 22, 2023 with English translation in Chinese Patent Application No. 2022103753977, 11 pages.

China Patent Office, Office Action dated Jun. 12, 2024 with English translation in Chinese Patent Application No. 2022103753977, 12 pages.

\* cited by examiner

ELECTRICAL CATHETER

RELATED APPLICATIONS

This application is a continuation of and claims priority to U.S. patent application Ser. No. 17/348,571 filed Jun. 15, 2021 entitled Electrical Catheter, which is a continuation of and claims priority to U.S. patent application Ser. No. 15/901,720 filed Feb. 21, 2018 entitled Electrical Catheter (now U.S. Pat. No. 11,083,872 issued Aug. 10, 2021), which claims benefit of and priority to U.S. Provisional Application Ser. No. 62/461,673 filed Feb. 21, 2017 entitled Electrical Catheter, all of which are hereby incorporated herein by reference in their entireties.

BACKGROUND OF THE INVENTION

Catheters are utilized in many interventional procedures as a conduit used to deliver a variety of therapeutic agents such as medical devices to a treatment site. While some catheters are configured as simple tubular conduits that passively deliver therapeutic agents and/or devices, other catheters are further configured with components requiring electrical power.

For example U.S. Pub. No. 2016/0345904, which is hereby incorporated by reference, discloses a catheter having one or more sensors and related circuitry at its distal end. These sensors can include pressure or temperature sensors, among others, for measuring conditions within a patient's vascular system. The body of the catheter is constructed with a layer of braided wires, some of which are used to conduct electrical current between the sensors and a proximal end of the catheter.

In another example U.S. Pub. No. 2015/0173773, which is hereby incorporated by reference, discloses a catheter with various electrical mechanisms for detaching a distal end of a catheter. In one embodiment, electrical wires within the catheter body supply electrical current to heater coils located near the catheter's distal end. When current is supplied, the heater coils activate to melt or break a portion of the catheter and releasing its distal end.

In yet another example U.S. Pat. No. 9,808,599, which is hereby incorporated by reference, discloses a catheter having electrical contacts within the interior passage of the catheter. Electrical current can be delivered to these contacts to cause a segmented implant within the catheter to separate or a bimetal guidewire to curve in a specific direction.

SUMMARY OF THE INVENTION

In one embodiment, a powered catheter and/or powered catheter system is described. The catheter includes a catheter hub with one set of contact components that are configured to connect to a mating cable with a corresponding second set of contact components. The mating cable can be part of another device, such as a controller or power source.

In one embodiment, a powered catheter and/or powered catheter system is described. The catheter includes a catheter hub with one set of contact components, and a number of wires connected to the catheter hub which connect to a distal portion of the catheter. The catheter hub contact components are configured for connection to a mating cable with a corresponding second set of contact components. The mating cable can be part of another device, such as a controller or power source. The interface between the mating cable and the catheter hub can be used to transfer current, signals, and/or or data from the device which the mating cable is connected to a distal portion of the catheter.

In one embodiment, a data transfer system is described which enables communication between a catheter and an external device. The catheter includes a hub with a first set of contact components. The data transfer system includes a mating cable with a second set of contacts; the mating cable connects the external device to the catheter hub and allows a signal or data to pass between the catheter hub and the external device. The catheter can include wires to transfer the signal or data from the catheter hub to another portion of the catheter.

In one embodiment, a powered catheter hub is described. The powered catheter hub includes one or more contact components.

In one embodiment, a powered catheter and/or powered catheter system is described. The powered catheter includes a catheter hub with one or more contact components, and one or more wires connected to the catheter hub which are configured to carry data or a signal from the catheter hub to another portion of the catheter.

In one embodiment, a detachment system for a therapeutic device (e.g. embolic coils) is described. The detachment system includes an external grip assembly. A mating cable connects the external grip assembly to a catheter hub, where the catheter hub and mating cable are each configured with contacts such that signals or data are transferred between the external grip assembly and the catheter hub. A series of wires are connected to the catheter hub such that data or signals can be transferred from the catheter hub to a distal portion of the catheter. The proximal end of a therapeutic device can be placed within the external grip assembly, and the external grip assembly can communicate with a distal portion of the catheter to convey a detachment sequence in order to detach a portion of the therapeutic device.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
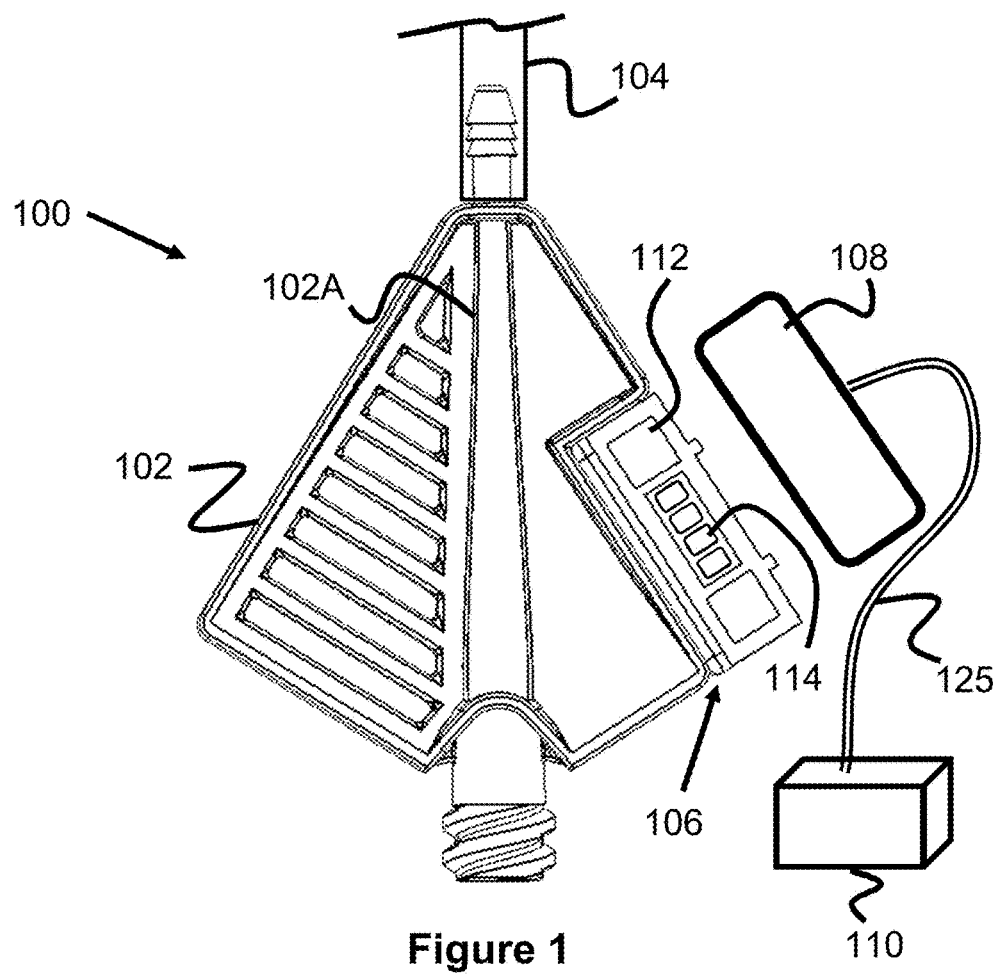
FIG. 1 is a catheter hub with a connection assembly according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Catheters are utilized in many interventional procedures as a conduit used to deliver a variety of therapeutic agents such as medical devices to a treatment site. While some catheters are configured as simple tubular conduits that passively deliver therapeutic agents and/or devices, other catheters are further configured with components requiring electrical power.

The following embodiments are directed to a system for conveying power and/or data between a catheter and a power interface. This system can allow for a variety of different catheter functionalities, including electrically interacting with therapeutic devices delivered through said catheter, providing imaging, or providing sensor information about a treatment area.

Since catheters are often used in interventional procedures, fluids such as blood and saline can be present. Since liquid exposure can affect or otherwise interrupt a circuit path, it is important to isolate the electrically conductive components. However, catheters are typically connected to a power/data interface either prior to or during a procedure, and therefore should include an electrical connector that is both easy to use and that resists fluid infiltration to its electrical contacts. The following embodiments address these issues. It should be further noted that while several different embodiments are described below, individual features of these components can also be used on other disclosed embodiments. In other words, each of the individual features described can be mixed and matched on any of the various embodiments.

FIG. 1 illustrates an electrical catheter system 100 that conveys electrical current and/or data between an electrical interface 110 and a catheter 104. The electrical interface 110 includes a wire 125 that terminates with an interface connector assembly 108, which in turn connects to a catheter connector assembly 106 on a catheter hub 102, allowing the power/data exchange with the hub 10. Wires 120 (FIG. 5) in the hub 102 are connected to an electrical path within the body of the catheter 104, allowing for the electrical interface 110 to convey power/data to the distal end of the catheter 104.

As described further in this specification, the interface connector assembly 108 and catheter connector assembly 106 may include magnetic attachment mechanisms, frictional/mechanical attachment mechanisms, or combinations of both. The embodiment shown in FIGS. 1-10 illustrates a primarily magnetic attachment mechanism. Specifically, the catheter connector assembly 106 includes two horizontally-facing magnets 112 and a single vertically-facing magnet 113 (seen in FIGS. 2-3). The interface connector assembly 108 (seen in FIGS. 9-10) similarly includes two horizontally-facing magnets 115 and a vertically-facing magnet 123. The spacing and orientation of the magnets 115, 123 is the same as magnets 112, 113, allowing the magnets to align and contact each other. If the magnets 112, 113 have opposite facing polarities to magnets 115, 123, they will magnetically engage each other with sufficient force to resist fluid penetration. While this specification refers to both the interface and catheter connector assemblies 108, 106 as having magnets, it should be understood that each corresponding magnet pair (e.g., magnets 113 and 123) can alternately be composed of only one magnet and one ferrous metal, which similarly provide magnetic attraction.

Figure 2:
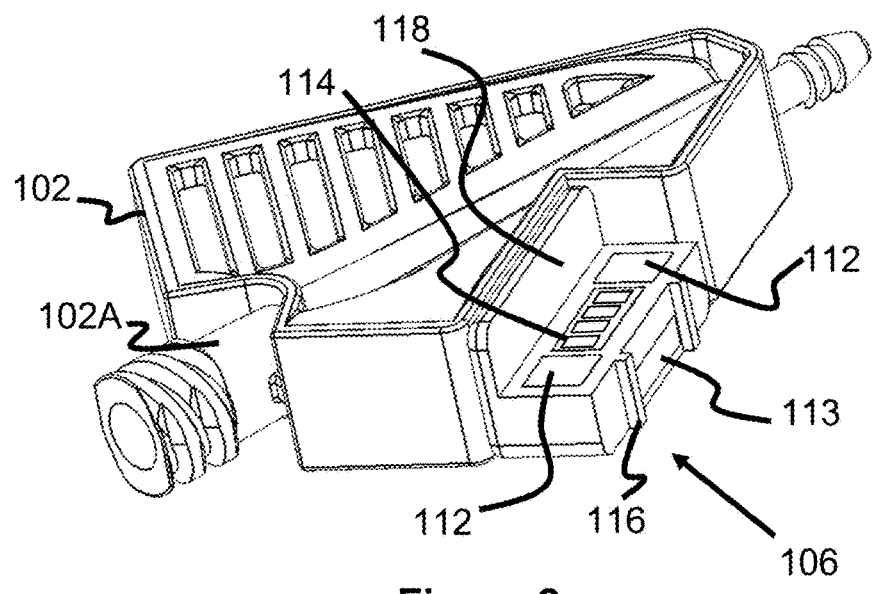
FIG. 2 is a catheter hub with a connection assembly according to the present invention.
Figure 3:
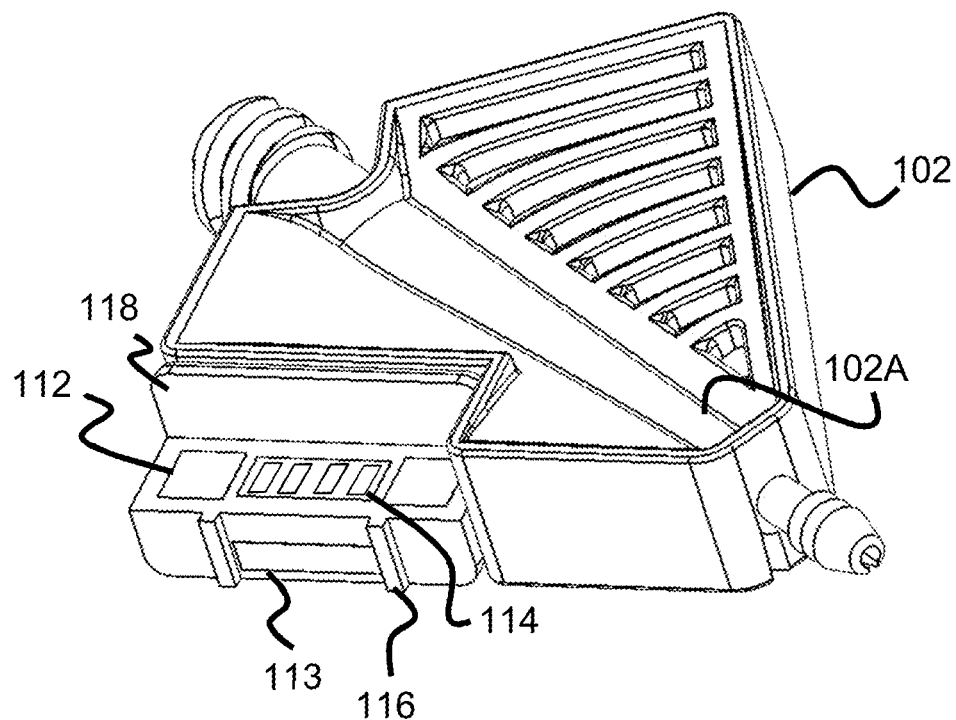
FIG. 3 is a catheter hub with a connection assembly according to the present invention.
Figure 4:
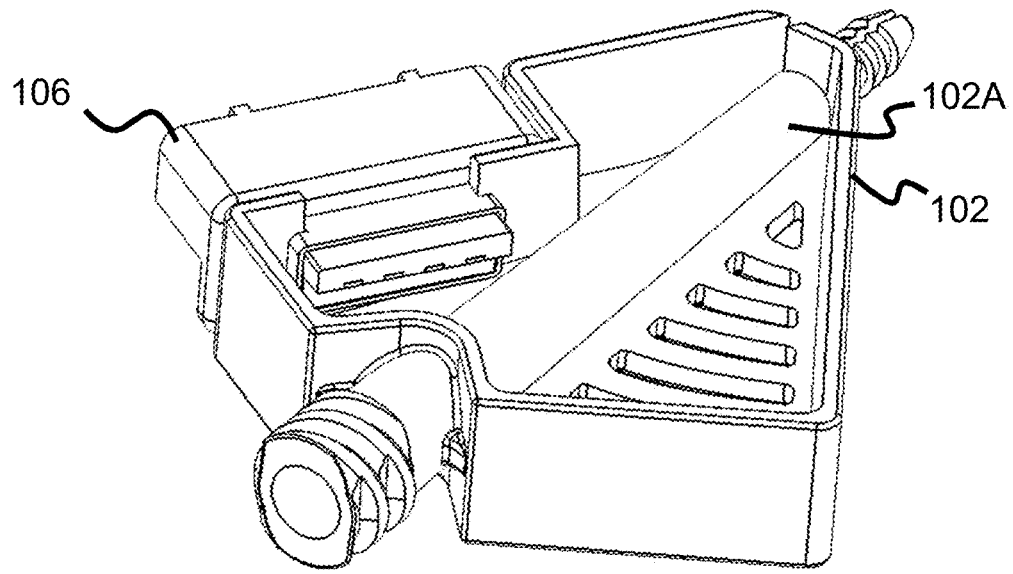
FIG. 4 is a catheter hub with a connection assembly according to the present invention.

As best seen in FIGS. 2 and 3, the catheter connector assembly 106 is recessed relative to the top surface of the catheter hub 102, creating a backstop or backwall 118 that the interface connector assembly 108 is positioned against. In one embodiment, the interface connector assembly 108 has a thickness that renders it relatively flush with the top surface of the catheter hub 104.

In the present embodiment, the catheter connector assembly 106 only includes a single sidewall adjacent to the backwall 118. To help prevent the interface connector assembly 108 from sliding sideways (i.e., to the left when facing the backwall 118), the lower vertical surface of the catheter connector assembly 106 includes two vertical ridges 116 on either side of the magnet 113. These ridges 116 mate with two similarly sized/positioned grooves 121 within an elevated portion 119 of the interface connector assembly 108. Optionally, these grooves 121 can be sized and otherwise configured to provide some friction with the ridges 116 when engaged to help frictionally retain the interface connector assembly 108 on the catheter connector assembly 106.

When the interface connector assembly 108 is properly connected to the catheter connector assembly 106, a plurality of catheter electrical contacts 114 are aligned and put into contact with a plurality of interface electrical contacts 117. The present embodiment depicts four contacts 114 that contact another four contacts 117 to exchange power and/or data signals between the catheter 104 and the interface 110. However, other numbers of contacts on each assembly 106,108 are also possible, depending on the functionality of the catheter 104. For example, 2, 3, 4, 5, 6, 7, and 18 individual contacts are possible.

Figure 5:
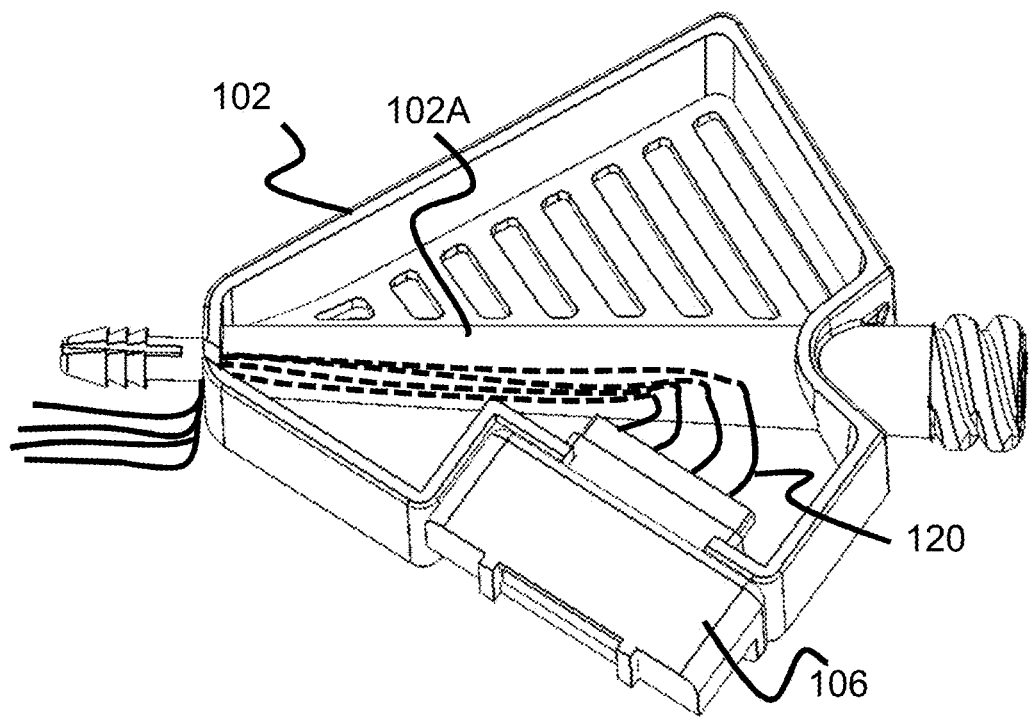
FIG. 5 is a catheter hub with a connection assembly according to the present invention.
Figure 6:
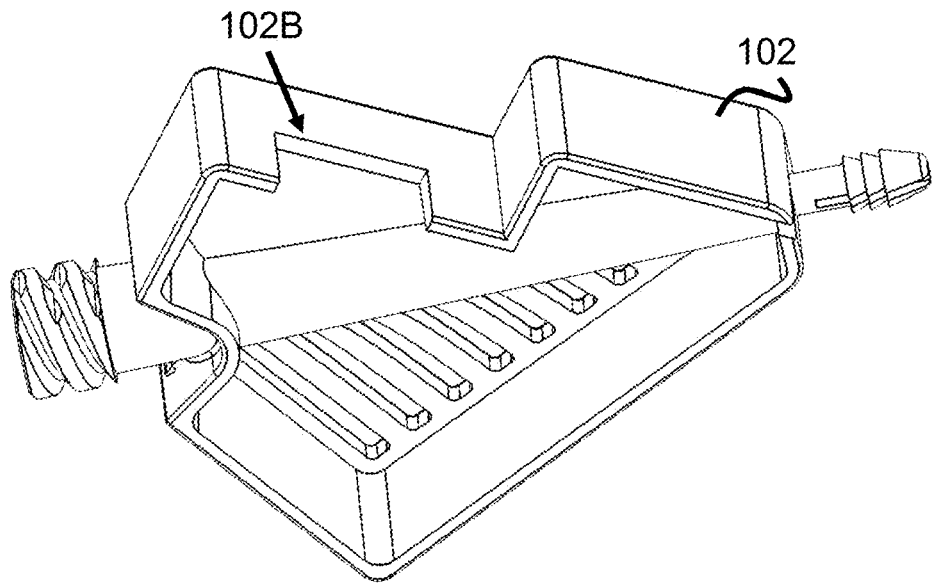
FIG. 6 is a catheter hub with a connection assembly according to the present invention.
Figure 7:
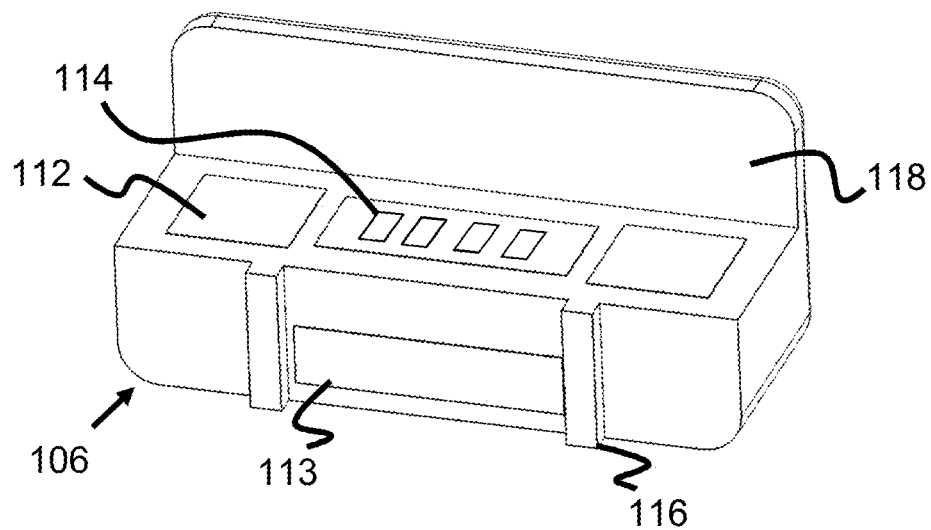
FIG. 7 is a catheter connection assembly according to the present invention.
Figure 8:
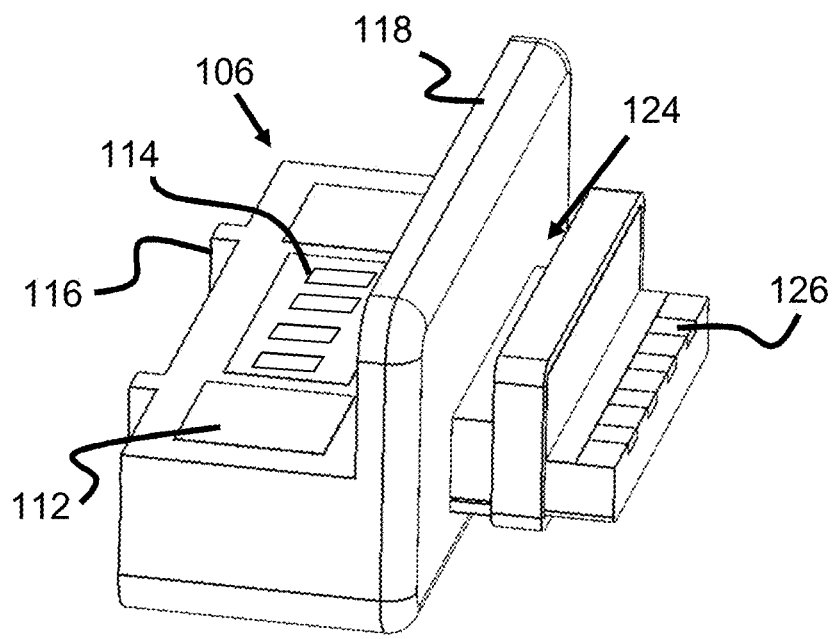
FIG. 8 is a catheter connection assembly according to the present invention.
Figure 9:
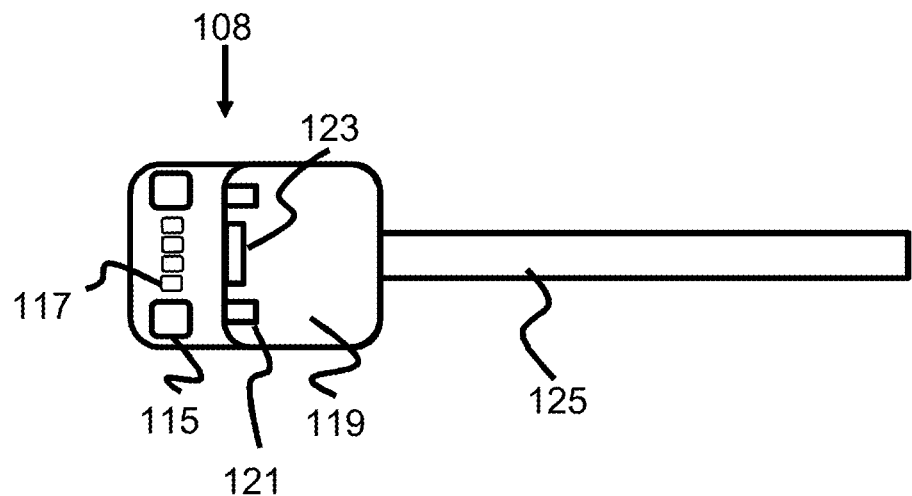
FIG. 9 is an interface connection assembly according to the present invention.
Figure 10:
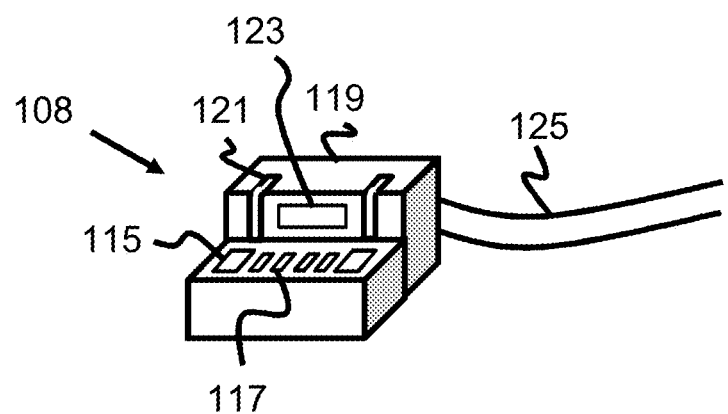
FIG. 10 is an interface connection assembly according to the present invention.

As seen best in FIGS. 5 and 8, the catheter connector assembly 106 includes a plurality of rear, internal electrical contacts 126 that are in electrical communication with contacts 114. A plurality of wires 120 are individually connected to those rear internal contacts 126 and extend through the hub 102 (optionally within the wall of the hub passage 102A) and into the catheter 104.

Figure 16:
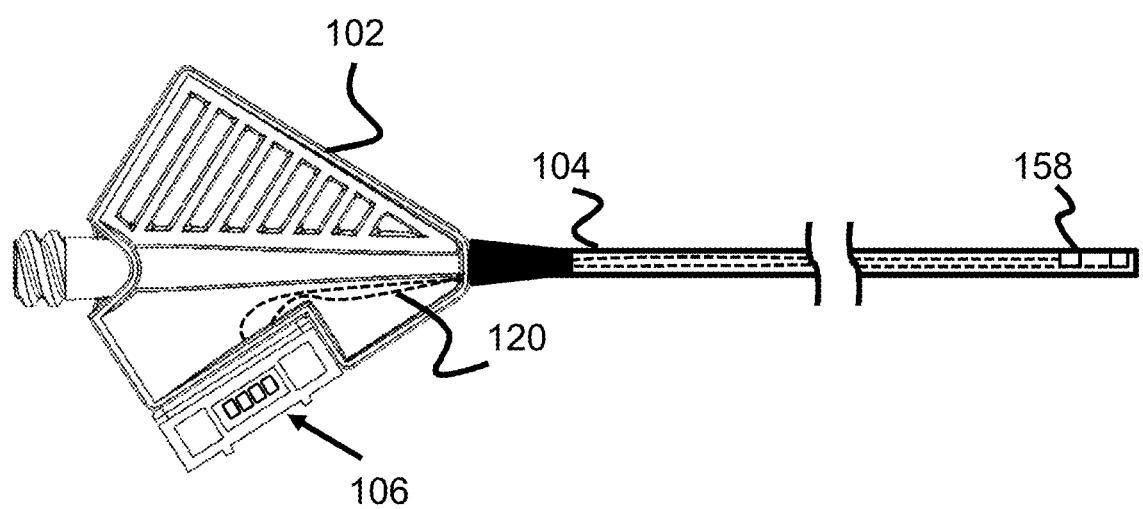
FIG. 16 is a catheter hub with a connection assembly according to the present invention.
Figure 17:
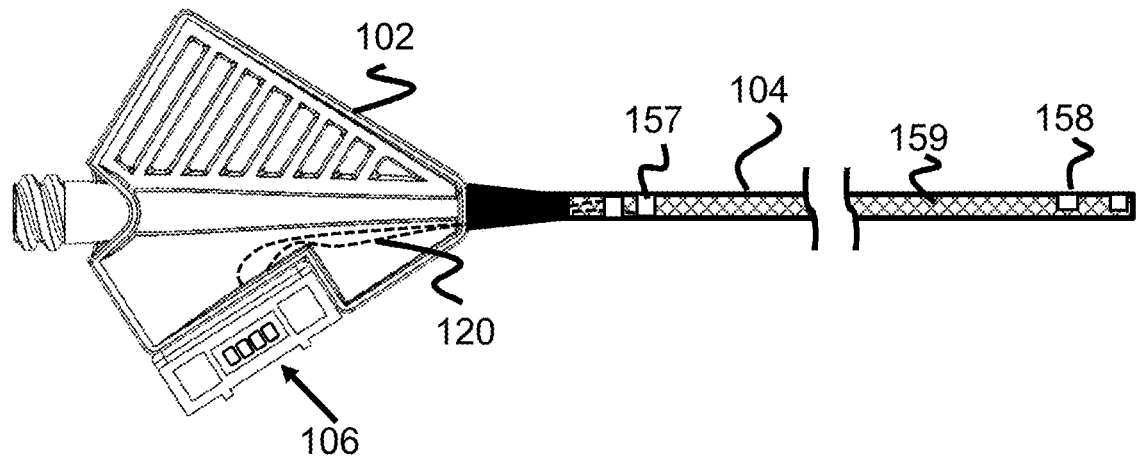
FIG. 17 is a catheter hub with a connection assembly according to the present invention.
Figure 18:
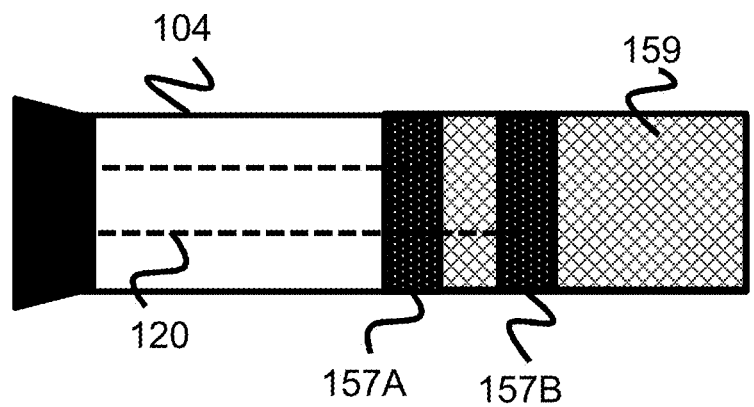
FIG. 18 is a catheter hub with a connection assembly according to the present invention.

In one embodiment shown in FIG. 16, the wires 120 extend within the wall of the catheter 104 to its distal end, connecting to electrically powered components 158 (e.g., a heater coil, sensors, etc.). In another embodiment shown in FIG. 17 and the magnified view of FIG. 18, each of the wires 120 are electrically connected to a conductive band 157 that is located within the wall of the catheter. The conductive bands 157 can be tubular structures that completely or partially encircle the catheter 104. Each band 157 is then electrically connected to one or more wires of a braided structural layer 159 within the wall of the catheter 104. These braided wires of the braided structural layer 159 are ultimately connected to one or more of the distal electrically powered components 158 (e.g., a heater coil, sensors, etc.) and provide electrical communication between the proximal and distal ends of the catheter. Additional details of using the braided structural layer of a catheter for conveying power and data can be found in U.S. Pub. No. 20160345904 which is hereby incorporated by reference. Additional details of electrically powered components can be found in U.S. Pat. No. 9,808,599, U.S. Pub. No. 2015/0173773, and 2016/0345904; all of which are incorporated herein by reference.

As discussed above, the powered catheter hub can be used as part of a broader electrical communication system enabling communication between an external interface connected 110 to the catheter hub via interface connector 108, and a distal end of the catheter. For example, the distal end of the catheter can include a pair of polarized contacts which electrically interact with an implant (e.g., embolic coil) delivery system. External interface 110 can include a battery which provides the voltage source and connects to the polarized contacts on the catheter through the interface connector 108 and catheter connector 106. The embolic coil delivery system includes a pair of conductive sleeves which align with the polarized catheter contacts to complete a circuit, thereby supplying current to a heater on the coil pusher to detach the coil from the coil pusher. Where four catheter connector contacts 114 and four corresponding interface connector contacts 117 are used, two contacts can be used for the positive and negative DC battery source leaving two additional contacts either for redundancy, or to power another distal catheter system (e.g., imaging system, pressure or temperature monitoring, ablation system, etc.), or as a feedback loop to confirm that detachment has taken place. In this way, the multiple contacts allow for multiple catheter processes to take place, or alternatively allow for redundancy to guard against failure, or allow for confirmation via a feedback loop. Obviously, more contacts (e.g., more than 4 contacts) would facilitate more catheter operations or more redundancy. Though this example primarily highlighted an illustrative concept for an embolic coil detachment system, various other catheter operations (e.g., imaging, pressure/temperature sensing, ablation, cooling, measurement, detachment system for detaching the distal tip of the catheter, etc.) are also possible. In various other examples, two of the connector contact points can provide electrical communication for current, data, or signals while two of the other connector contacts points can act like a capacitor for various purposes (e.g., low power sensing). Additionally, the two distal catheter contacts can further be combined with a distal capacitor system for a catheter-mounted low power sensing application.

In other examples, external interface 110 is a broader computing system or "brain" that computationally sends signals to a distal portion of the catheter or interprets received signals from the distal portion of the catheter. For example, the external interface 110 could be used to send acoustic signals outside of the catheter to then recreate and display an image of the target therapeutic area based on recreating an image from the received acoustic signals. For another example, the external interface or "brain" would use resistance or other measurements to determine when an embolic coil detachment contacts are aligned correctly with the catheter's contacts, convey a signal (e.g., a light) to the user, and the user would take an action (e.g., press a button) on the external interface to send an impulse to the distal end of the catheter to detach the coil.

Figure 19:
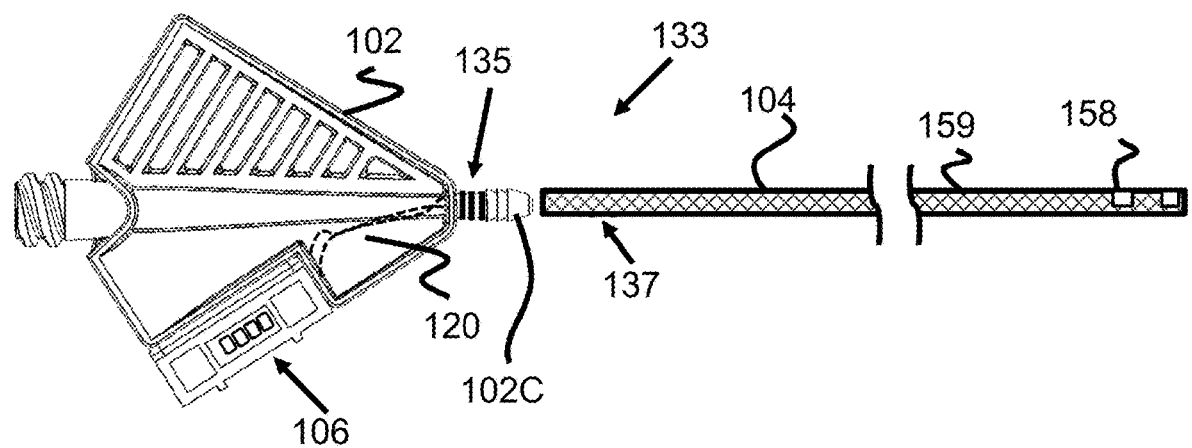
FIG. 19 is a catheter hub with a connection assembly according to the present invention.
Figure 20:
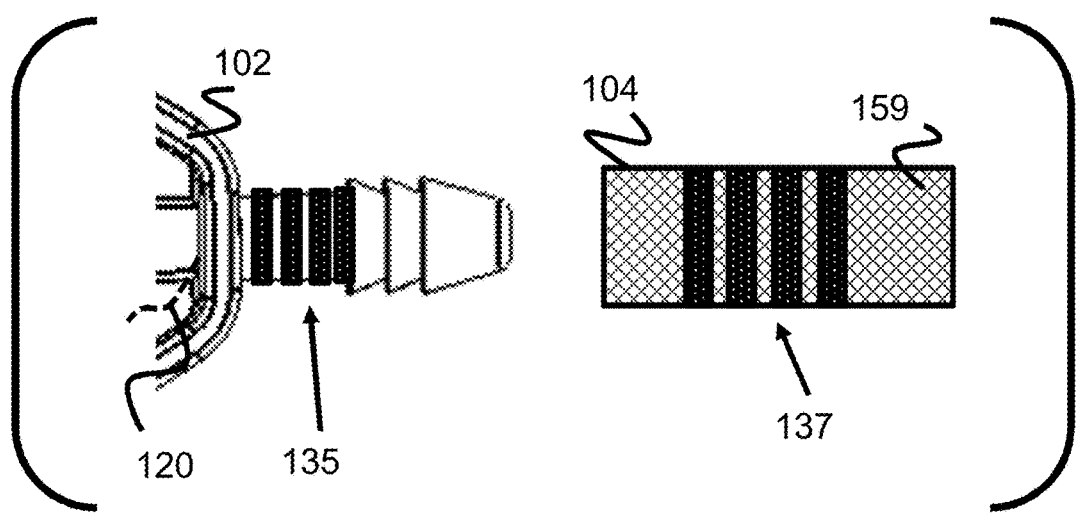
FIG. 20 is a catheter hub with a connection assembly according to the present invention.

In another embodiment shown in FIGS. 19 and 20, the hub 102 and catheter 104 can have a standardize electrical connection assembly 133. More specifically, the wires 120 connect to a plurality of tubular electrical contacts 135 on the distal end 102C of the hub 102. Similarly, the catheter 104 also includes a plurality of tubular electrical contacts 137 within its inner passage that are positioned to align with contacts 135. Thus, when the proximal end of the catheter 104 is placed over the distal end 102C of the hub 102, the contacts 135 and 137 contact each other and establish an electrical communication between the distal electrically powered components 158 (via the braided structural layer 159) and the hub 102. The numbering and positioning of the contacts 137, 137 can be standardized such that the hub 102 can be used with a variety of catheters with different electrically powered components 159. Optionally, the hub 102 may further include circuitry that communicates a unique identification (e.g., a serial number) that can be used for tracking and inventory purposes, as described elsewhere in this specification.

Referring to FIGS. 4-8, the hub 102 of the present embodiment can have a generally hollow body, allowing the catheter connector assembly 106 to be connected to the hub 102 as a separate, discrete component to facilitate the manufacturing process (note, these figures illustrate the hub 102 with a bottom panel removed just for illustration purposes so the catheter connector assembly 106 can be seen more clearly). For example, the body of the hub 102 can include a recessed area 102B in a side wall that can engage a groove 124 adjacent the backwall 118 of the catheter connector assembly 106. Alternately, the hub 102 can be a single, solid, unitary component (except for the hub passage 102A). For example, such a hub could be created via injection molding around the wires 120 in an injection molding mold, or designing a mold with wire passages positioned within it. The shape of the catheter connector assembly 106 can be either part of the mold or attached to the hub after the molding process.

Figure 11:
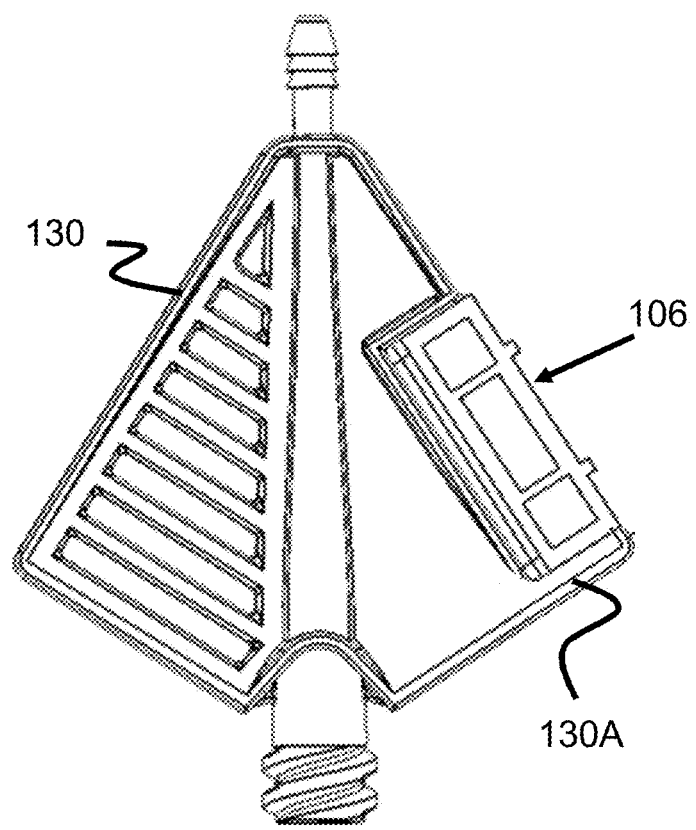
FIG. 11 is a catheter hub with a connection assembly according to the present invention.

The catheter connector assembly 106 can be located at a number of positions on the catheter hub. For example, FIG. 11 illustrates a catheter hub 130 in which the catheter connector assembly 106 is positioned further distally relative to the prior-described catheter hub 102. Since the catheter connector assembly 106 is recessed relative to the top planar surface of the hub 130, the distal positioning creates a proximal sidewall portion 130A. Hence, the interface connector assembly 108 is provided lateral support from both sides when connected to the catheter connector assembly 106.

Figure 12:
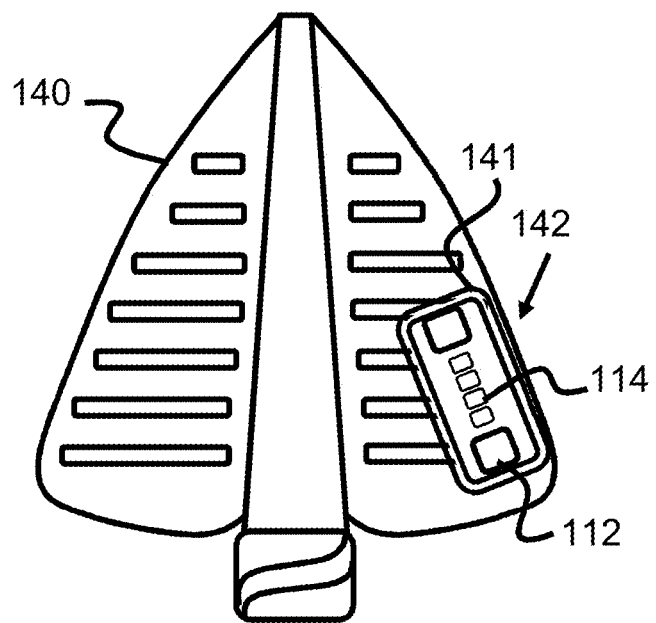
FIG. 12 is a catheter hub with a connection assembly according to the present invention.
Figure 13:
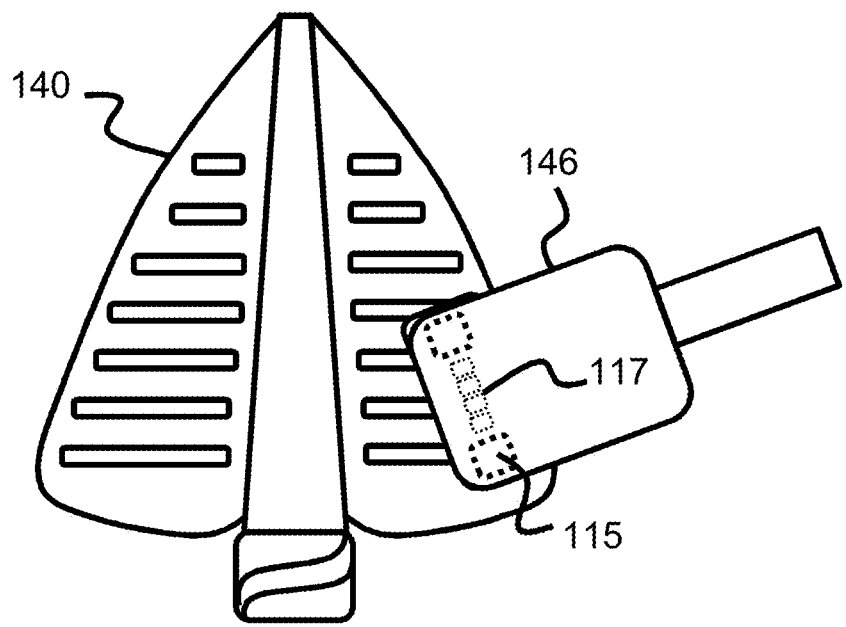
FIG. 13 is a catheter hub with a connection assembly according to the present invention.
Figure 14:
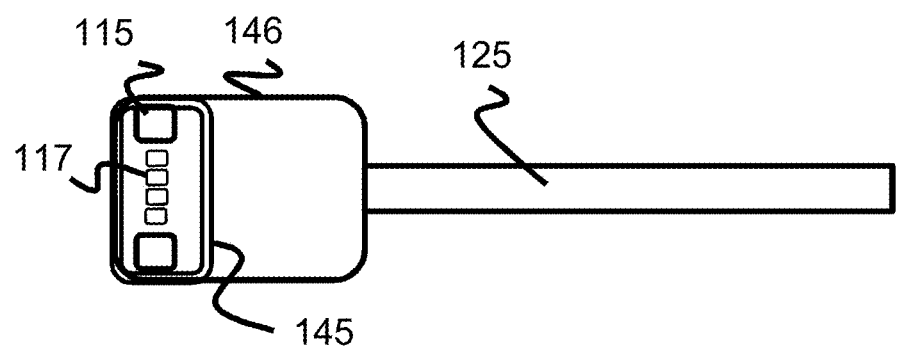
FIG. 14 is an interface connection assembly according to the present invention.

FIGS. 12 and 13 illustrate another embodiment of a catheter hub 140 that has a generally rounded body shape and a catheter connector assembly 142 that is positioned on a top surface of the hub 140. Unlike the prior assembly 106, the present assembly 142 is not substantially recessed and includes generally horizontal surfaces for connection purposes. Hence, the assembly 142 only includes two magnets 112 on either end of the electrical contacts 114 that mate with similarly positioned magnets 115 and electrical contacts 114 on the interface connector assembly 146, seen in FIGS. 13-14. Further, to help prevent entry of fluid during a procedure, the catheter connector assembly 142 includes a depression or channel 141 that extends entirely around the perimeter of the assembly. Optionally, as seen in the bottom view of the interface connector assembly 146 in FIG. 14, a ridge or resilient seal 145 can be included to mate with the channel 141 when connected.

Figure 15:
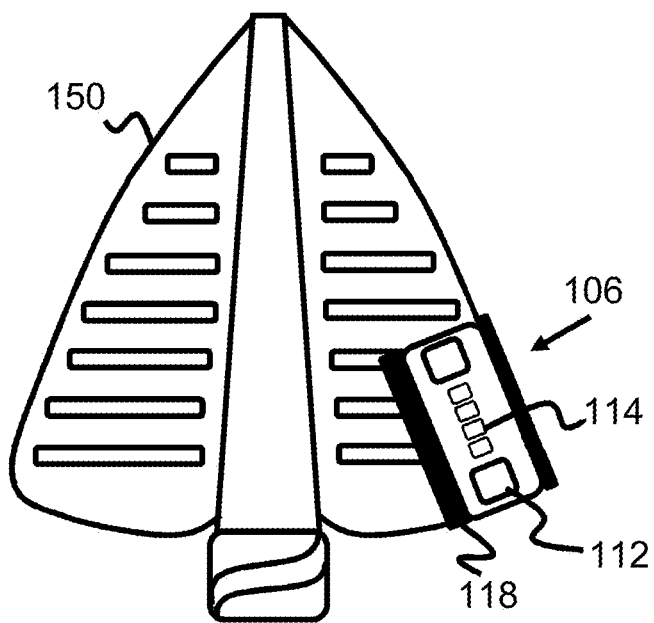
FIG. 15 is a catheter hub with a connection assembly according to the present invention.

FIG. 15 illustrates a catheter hub 150 that has a curved body style similar to the hub 140 of FIGS. 12 and 13, but further includes a recessed catheter connector assembly 106 similar to that of FIGS. 1-10.

Figure 21:
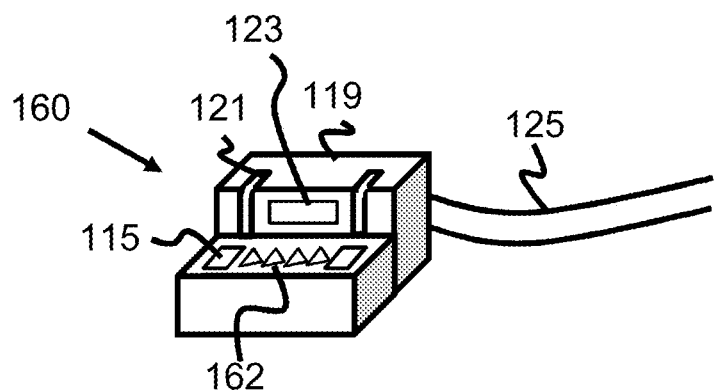
FIG. 21 is an interface connector assembly according to the present invention.
Figure 26:
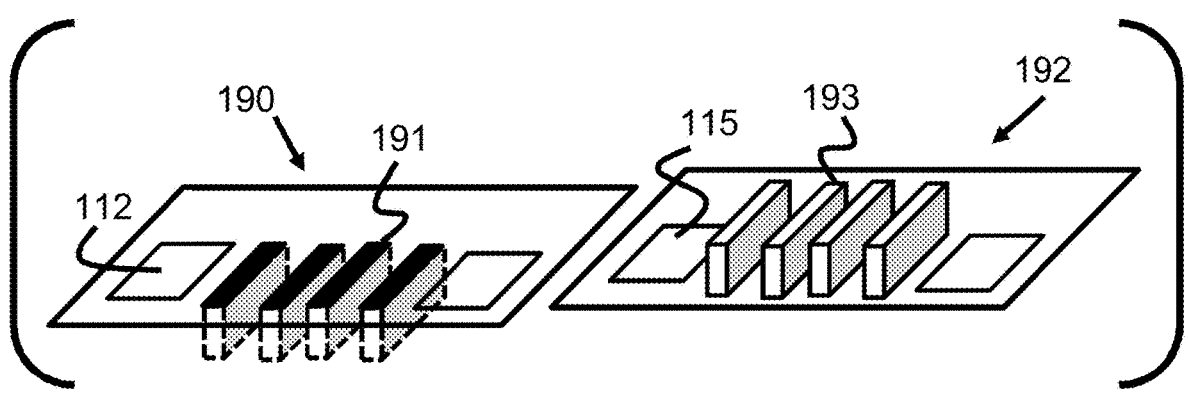
FIG. 26 is an interface connector assembly according to the present invention.

While the electrical contacts on either the interface connector assembly or the catheter connector assembly can be flat, either of these contacts can also be raised. For example, FIG. 21 illustrates an interface connector assembly 160 that has electrical contacts 162 that are triangular or upwardly "pointed" to help ensure physical contact. In another embodiment, the contacts can have a raised, curve shape to provide some spring force to further facilitate contact. In another example, FIG. 26 illustrates a catheter connector assembly 190 having a plurality of recessed, rectangular electrical contacts 191 and an interface connector assembly 192 having a plurality of raised, rectangular electrical contacts 193. Any contact interface shapes or types known in the connector art, including those utilized in USB-type communication systems can be used to facilitate communication between the catheter connector assembly 106 and the interface connector assembly 108. To this end, catheter connector assembly contacts 114 and interface connector assembly 117 can utilize male projecting/female receiving data connection interfaces, or various pin connector concepts such as spring-pins, etc.

Figure 22:
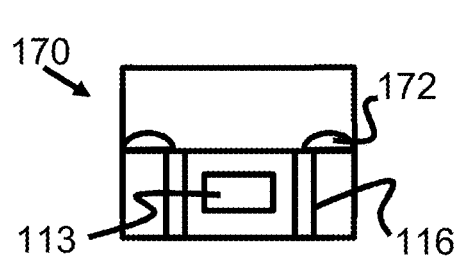
FIG. 22 is an interface connector assembly according to the present invention.
Figure 23:
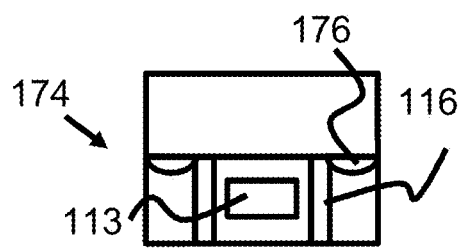
FIG. 23 is an interface connector assembly according to the present invention.

The magnets of the interface connector assembly and/or the catheter connector assembly can be flat, an elevated shape, or a depressed shape. For example, FIG. 22 illustrates an interface connector assembly 170 in which the magnets 172 have a raised, rounded shape, while FIG. 23 depicts an interface connector assembly 174 having depressed or downwardly rounded magnets 176. Preferably, the catheter connector assembly includes magnets or ferrous material having an opposite shape to allow the structures to mate to each other.

Figure 24:
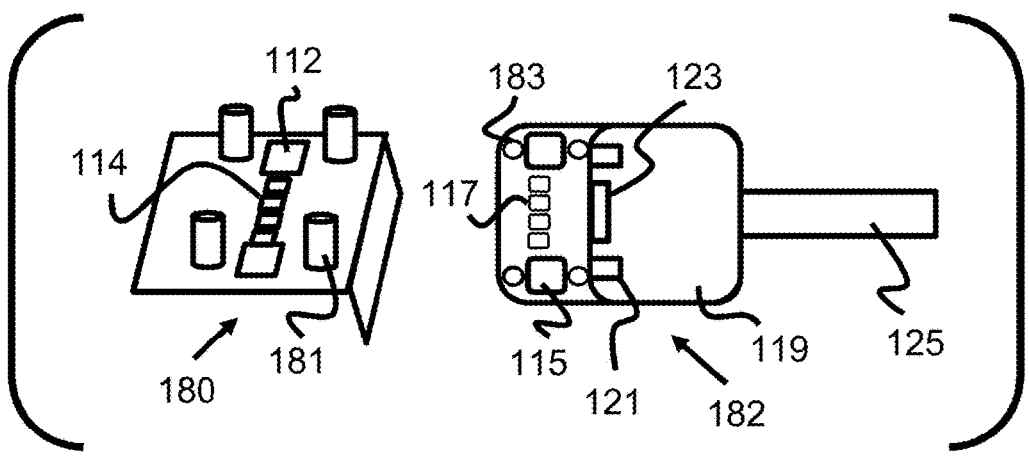
FIG. 24 is an interface connector assembly according to the present invention.
Figure 25:
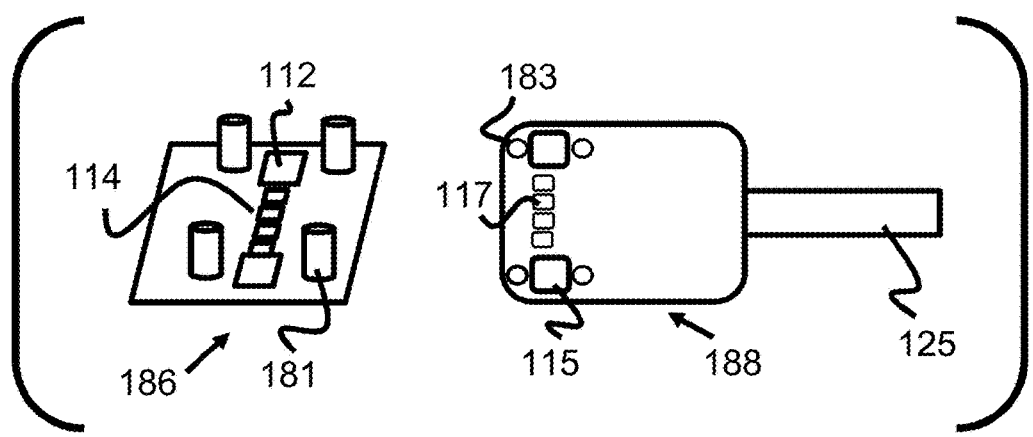
FIG. 25 is an interface connector assembly according to the present invention.

The catheter connector assembly and the interface connector assembly can include structures that frictionally engage each other, either in addition to the magnets or instead of the magnets. For example, FIG. 24 or 25 illustrate a catheter connector assembly 180/186 having four cylindrical posts 181 positioned near the magnets 112. Corresponding holes 183 on the interface connector assembly 182/188 are sized to accept the posts 181 and provide frictional engagement. While cylindrical posts are illustrated, other shapes are possible, such as triangular, rectangular, or hexagonal.

Figure 27:
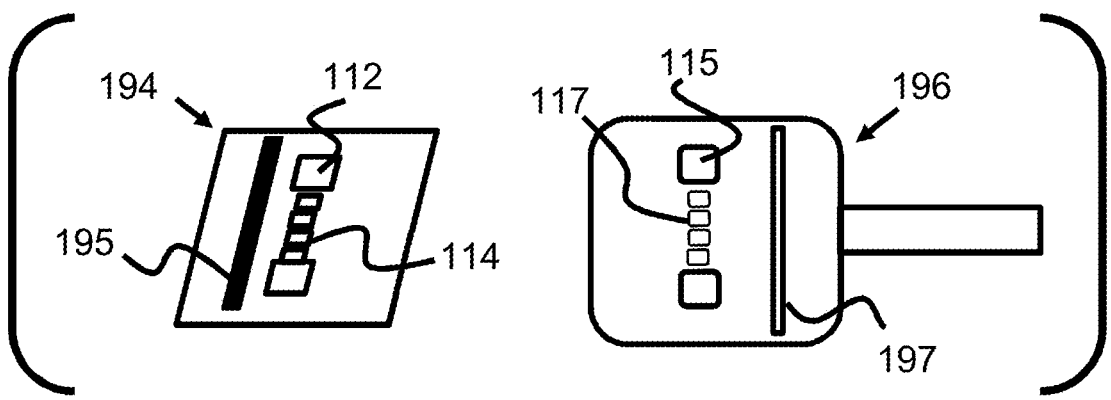
FIG. 27 is an interface connector assembly according to the present invention.
Figure 28:
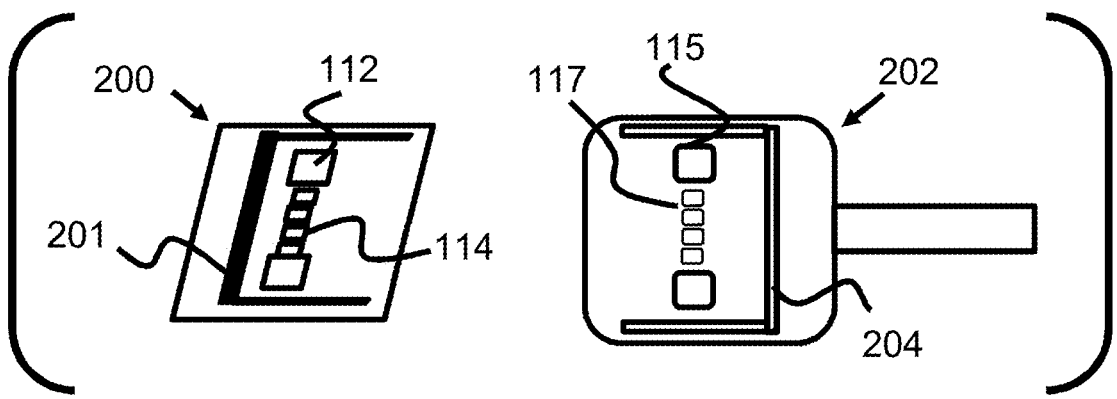
FIG. 28 is an interface connector assembly according to the present invention.

In addition to the use of magnets and/or fictional engagement structures, other connector shapes can additional be used to help prevent fluid from reaching the electrical contacts. For example, FIG. 27 illustrates a catheter connector assembly 194 with a single elongated channel 195 extending along the length of both the contacts 114 and magnets 112. A raised ridge 197 on the interface connector assembly 196 may also be included to mate with the channel 195 and further seal the connectors. FIG. 28 illustrates a similar embodiment that includes a catheter connector assembly 200 having a "C" shaped channel 201 and an interface connector assembly 202 having a corresponding "C" ridge 204 that mates with the channel 201.

Figure 29:
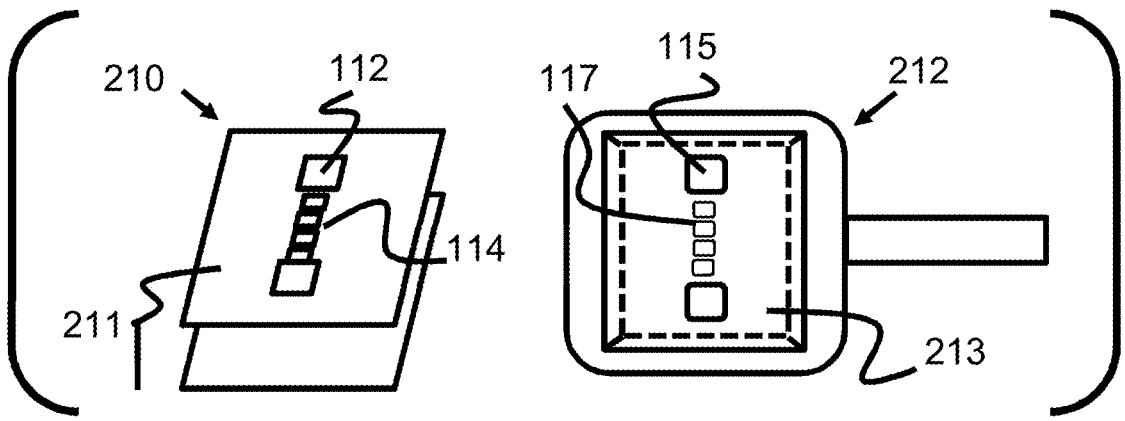
FIG. 29 is an interface connector assembly according to the present invention.
Figure 30:
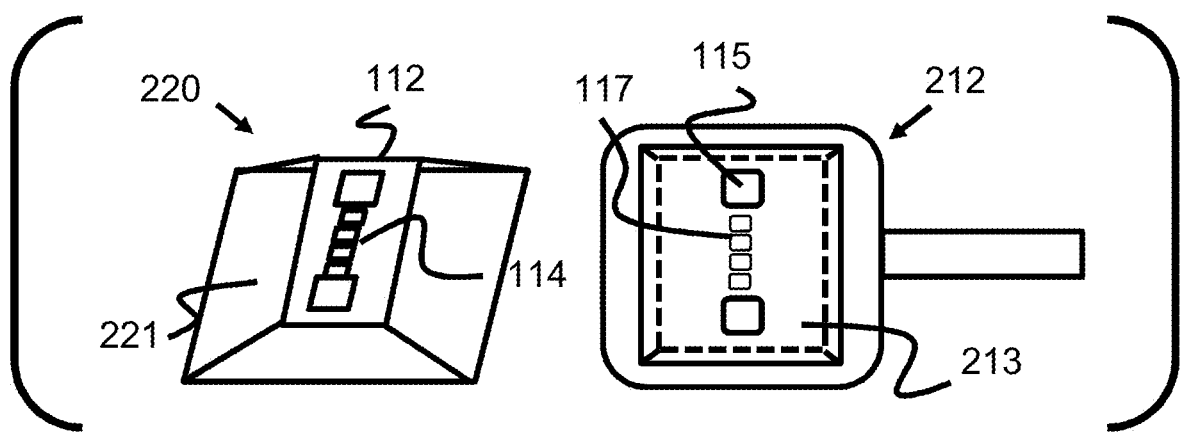
FIG. 30 is an interface connector assembly according to the present invention.
Figure 31:
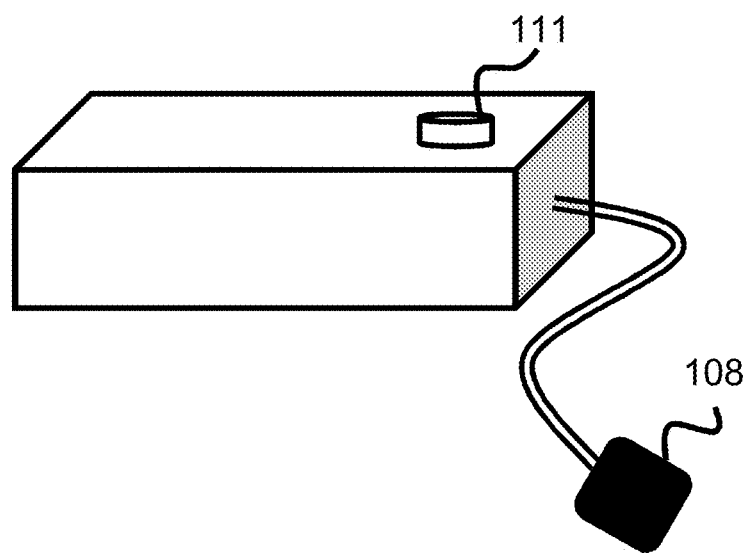
FIG. 31 is an interface connector assembly according to the present invention.

FIG. 29 illustrates a catheter connector assembly 210 having a generally rectangular, raised shape 211, while an interface connector assembly 212 includes a rectangular depressed region 213 that fits over the raised shape 211. The rectangular, raised shape 211 elevates the contacts 114 to minimize fluid infiltration during a procedure. FIG. 30 illustrates a similar, raised catheter connector assembly 220 having downwardly-angled sides 221 and an interface connector assembly 212 having a depression with similar, mating, angled sides. Again, this shape helps elevate the contacts 114 to prevent fluid infiltration and provides a sloped surface to move fluid away from the contacts 114 during a procedure. Alternatively, only one side of the catheter connector assembly is sloped—for instance, only the side of the connector closer to the outward edge of the catheter hub is sloped in order to move fluid away from the connector assembly/catheter hub body.

In another embodiment, a hydrophobic coating can be applied to the regions surrounding the electrical contacts and the magnets to help repel the ingress of fluid. For example, such a coating may include composite/nano-composite materials such as manganese oxide polystyrene, zinc oxide polystyrene, silica or fluoropolymer coatings. Such a coating may also include polymeric materials such as heptadecafluorohexyl-trimethoxysilane, polyhexafluoropropylene, polytetrafluoroethylene (PTFE); these polymeric coatings may be further engineered or chemically altered to further augment their hydrophobic properties.

Figure 32:
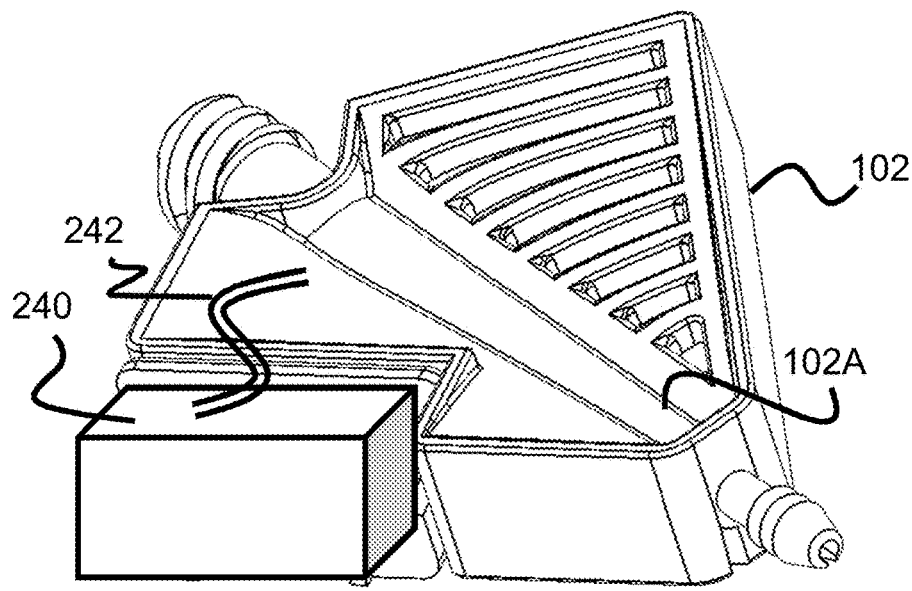
FIG. 32 is an interface connector assembly according to the present invention.

To further prevent the intrusion of fluid on the electrical contacts, the hub 102 may also include a cover 240 that is attached to the body of the hub 102 via a retaining filament 242, as seen in FIG. 32. Depending on the shape, the cover 240 may include various detents, channels, ridges, magnets, or other mechanisms to provide a retaining force. The catheter can be shipped with the cover to preserve electrical integrity during shipment. This cover could then be detached to facilitate electrical attachment, and later replaced over the connector assembly once the catheter's electrical connection functionality is no longer in use to help preserve the electrical integrity of the connector.

Figure 33:
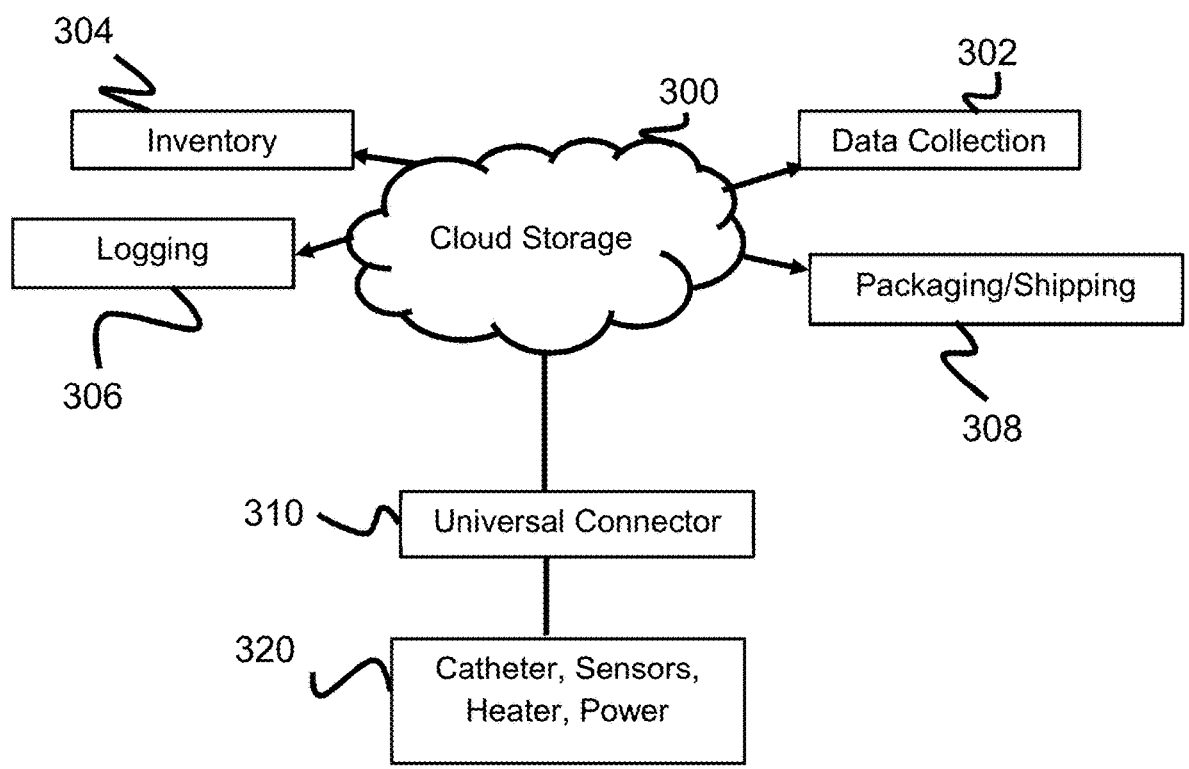
FIG. 33 is a view of a computer system configured to interact with an interface connector assembly.

As previously discussed with regard to FIGS. 19 and 20, the standardized electrical connection assembly 133 can be used to track data from the catheter 102 (e.g., via a serial number or similar identification code). Specifically, as seen in FIG. 33, the universal connector 310 can connect the catheter, sensors, heater, and power 320 to computer/cloud servers 300 to store in a database. Once in a database, the use of the catheter can be logged, recorded, and analyzed; stored in a catheter data collection 302, inventory 304, logging 306, and packing/shipping 308. Additionally, this system can be used to provide personalized patient information, where the external interface contains patient-specific data and the catheter system can utilize this patient specific data to perform a targeted procedure tailored to the patient. This data can be stored in the external interface, or the catheter connector can further contain a data receiving disk slot which the physician can use to input a disk or data interface containing targeted information about the patient, catheter, inventory, or other data type. Other variations of the catheter connector concept can utilize a wireless telemetry system where the catheter hub and external interface utilize wireless systems to communicate with each other.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A catheter hub, comprising:
a hub body;
a hub passage extending longitudinally between a proximal end and a distal end of the hub body; and
a catheter connector assembly integral with the hub body and exterior to the hub passage, the catheter connector assembly comprising a frictional engagement mechanism,
wherein the frictional engagement mechanism comprises a plurality of posts and a magnetic engagement mechanism between the plurality of posts.

2. The catheter hub of claim 1, wherein, in an engaged configuration, each of the plurality of posts engage with a hole on an interface connector assembly.

3. The catheter hub of claim 2, wherein the interface connector assembly is an electrical interface,
where in the engaged configuration, the electrical interface is in electrical connection with a plurality of wires, and
wherein the plurality of wires are electrically connected to an electrical path within a body of a catheter.

4. The catheter hub of claim 3, wherein the catheter further comprises a lumen in fluid communication with the hub passage of the hub body.

5. A catheter system, comprising:
a catheter hub comprising a hub body, a hub passage extending longitudinally between a proximal end and a distal end of the hub body, and a catheter connector assembly adjacent to the hub passage, wherein the catheter connector assembly comprises a frictional engagement mechanism; and
an interface connector assembly; and,
wherein, in an engaged configuration, the interface connector assembly of the interface connector assembly frictionally engages with the frictional engagement mechanism of the catheter hub;
wherein, in the engaged configuration, the interface connector assembly is in electrical communication with a catheter; and,
wherein the catheter comprises a lumen in fluid communication with the hub passage of the catheter hub.

6. The catheter system of claim 5, wherein the frictional engagement mechanism is comprised of a projection; wherein the interface connector assembly includes an indentation; and wherein, in the engaged configuration, the projection of the frictional engagement mechanism frictionally engages with the indentation of the interface connector assembly.

7. The catheter system of claim 5, wherein the frictional engagement mechanism is comprised of an indentation; wherein the interface connector assembly includes a projection; and wherein, in the engaged configuration, the indentation of the frictional engagement mechanism frictionally engages with the projection of the interface connector assembly.

8. A catheter hub, comprising:
a hub body;
a hub passage extending longitudinally between a proximal end and a distal end of the hub body; and
a catheter connector means adjacent to the hub passage, the catheter connector means comprising a frictional engagement means for frictionally engaging with an interface connection means; and,
wherein the frictional engagement means comprises an elongated C-shaped channel.

9. The catheter hub of claim 8, further comprising a magnetic engagement mechanism positioned within the elongated C-shaped channel.

10. The catheter hub of claim 8, further comprising a magnetic engagement mechanism adjacent to the elongated channel.

11. The catheter hub of claim 8, wherein, in an engaged configuration, a raised ridge of an interface connector assembly mates with the elongated channel.

12. A catheter hub, comprising:
a hub body;
a hub passage extending longitudinally between a proximal end and a distal end of the hub body; and
a catheter connector assembly integral with the hub body and exterior to the hub passage, the catheter connector assembly comprising a frictional engagement mechanism,
wherein the frictional engagement mechanism comprises a cylindrical, triangular, rectangular, or hexagonal projection.

13. The catheter hub of claim 12, wherein, in an engaged configuration, the rectangular projection engages with a rectangular depressed region of an interface connector assembly.

14. The catheter hub of claim 12, further comprising a magnetic engagement mechanism positioned on the rectangular projection.

15. The catheter hub of claim 12, wherein the rectangular projection includes downwardly-angled sides.

* * * * *